(12) United States Patent
Pan et al.

(10) Patent No.: US 11,801,323 B2
(45) Date of Patent: Oct. 31, 2023

(54) ABSORBENT ARTICLE WITH PHILIC ANHYDROUS LOTION

(71) Applicant: The Procter & Gamble Company, Cincinnati, OH (US)

(72) Inventors: Robert Ya-lin Pan, Cincinnati, OH (US); Debora Christine Ebert, Blanchester, OH (US); Peter Christopher Ellingson, Symmes Township, OH (US); Raphael Warren, Amberley Village, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 213 days.

(21) Appl. No.: 17/148,754

(22) Filed: Jan. 14, 2021

(65) Prior Publication Data

US 2021/0236685 A1    Aug. 5, 2021

Related U.S. Application Data

(63) Continuation of application No. 15/785,543, filed on Oct. 17, 2017, now Pat. No. 10,912,857, which is a (Continued)

(51) Int. Cl.
    *A61F 13/15* (2006.01)
    *A61L 15/20* (2006.01)
    *A61K 8/02* (2006.01)
    *A61K 8/25* (2006.01)
    *A61K 8/27* (2006.01)
    (Continued)

(52) U.S. Cl.
    CPC .......... *A61L 15/20* (2013.01); *A61F 13/8405* (2013.01); *A61K 8/0208* (2013.01); *A61K 8/25* (2013.01); *A61K 8/27* (2013.01); *A61K 8/31* (2013.01); *A61K 8/37* (2013.01); *A61K 8/39* (2013.01); *A61L 15/18* (2013.01); *A61L 15/34* (2013.01); *A61L 15/48* (2013.01); *A61Q 19/00* (2013.01); *A61F 2013/8455* (2013.01); *A61K 2800/10* (2013.01)

(58) Field of Classification Search
    CPC .......... A61L 15/20; A61L 15/18; A61L 15/34; A61L 15/48; A61F 13/8405; A61F 2013/8455; A61K 8/25; A61K 8/27; A61K 8/31; A61K 8/37; A61K 8/39; A61K 2800/10; A61Q 19/00
    USPC ........................................ 604/360, 359, 367
    See application file for complete search history.

(56) References Cited

U.S. PATENT DOCUMENTS 4,629,643 A    12/1986  Curro et al.
5,643,588 A    7/1997   Roe et al.
(Continued)

FOREIGN PATENT DOCUMENTS

JP    2004051505 A    2/2004
WO    WO 99/45771    *    9/1999    ............. A01N 25/34

OTHER PUBLICATIONS

All Office Actions, U.S. Appl. No. 15/785,543.
(Continued)

*Primary Examiner* — Jacqueline F Stephens
(74) *Attorney, Agent, or Firm* — Melissa G. Krasovec; William E. Gallagher

(57) ABSTRACT

A lotion composition is provided. The lotion composition includes a) about 1% to about 90%, by weight, of a rheology structurant; and a b) carrier.

2 Claims, 10 Drawing Sheets

Related U.S. Application Data continuation of application No. 14/563,509, filed on Dec. 8, 2014, now Pat. No. 9,808,551, which is a continuation of application No. 13/111,187, filed on May 19, 2011, now Pat. No. 8,921,640.

(60) Provisional application No. 61/391,353, filed on Oct. 8, 2010, provisional application No. 61/391,251, filed on Oct. 8, 2010.

(51) Int. Cl.
| | | |
|---|---|---|
| *A61K 8/31* | (2006.01) | |
| *A61K 8/39* | (2006.01) | |
| *A61L 15/34* | (2006.01) | |
| *A61L 15/48* | (2006.01) | |
| *A61Q 19/00* | (2006.01) | |
| *A61F 13/84* | (2006.01) | |
| *A61K 8/37* | (2006.01) | |
| *A61L 15/18* | (2006.01) | |

(56) References Cited

U.S. PATENT DOCUMENTS

| | | |
|---|---|---|
| 5,968,025 A | 10/1999 | Roe et al. |
| 6,409,713 B1 | 6/2002 | Osborn, III et al. |
| 6,426,444 B2 | 7/2002 | Roe et al. |
| 6,570,054 B1 | 5/2003 | Gatto et al. |
| 7,172,801 B2 | 2/2007 | Hoying et al. |
| 7,270,861 B2 | 9/2007 | Broering et al. |
| 7,410,683 B2 | 8/2008 | Curro et al. |
| 7,507,459 B2 | 3/2009 | Turner et al. |
| 7,521,588 B2 | 4/2009 | Stone et al. |
| 7,553,532 B2 | 6/2009 | Turner et al. |
| 7,626,073 B2 | 12/2009 | Catalan |
| 7,648,752 B2 | 1/2010 | Hoying et al. |
| 7,670,665 B2 | 3/2010 | Hoying et al. |
| 7,718,243 B2 | 5/2010 | Curro et al. |
| 7,732,657 B2 | 6/2010 | Hammons et al. |
| 7,785,690 B2 | 8/2010 | Turner et al. |
| 8,044,256 B2 | 10/2011 | Gatto et al. |
| 8,921,640 B2 | 12/2014 | Pan et al. |
| 9,669,130 B2 | 6/2017 | Pan et al. |
| 9,808,551 B2 | 11/2017 | Pan et al. |
| 10,912,857 B2 * | 2/2021 | Pan .................. A61K 8/37 |
| 2001/0025162 A1 * | 9/2001 | Roe .................. A61F 13/512 |
| | | 604/367 |
| 2002/0006434 A1 | 1/2002 | Shanklin et al. |
| 2005/0059941 A1 | 3/2005 | Baldwin et al. |
| 2005/0129651 A1 | 6/2005 | Gatto et al. |
| 2005/0137544 A1 | 6/2005 | Schroeder et al. |
| 2005/0208113 A1 | 9/2005 | Roe et al. |
| 2006/0134026 A1 | 6/2006 | Park et al. |
| 2006/0135920 A1 | 6/2006 | Virgilio et al. |
| 2007/0219515 A1 | 9/2007 | Marsh et al. |
| 2008/0287896 A1 | 11/2008 | Vega et al. |
| 2009/0155325 A1 | 6/2009 | Wenzel et al. |
| 2009/0197948 A1 | 8/2009 | Miyahara et al. |

OTHER PUBLICATIONS

All Office Actions, U.S. Appl. No. 13/111,187.
All Office Actions, U.S. Appl. No. 14/563,509.
International Search Report and Written Opinion; Application Ser. No. PCT/US2011/054907; dated May 7, 2012, 8 pages.

* cited by examiner

ABSORBENT ARTICLE WITH PHILIC ANHYDROUS LOTION

CROSS REFERENCE TO RELATED APPLICATIONS

This application is a continuation of, and claims priority under 35 U.S.C. § 120 to, U.S. patent application Ser. No. 15/785,543, filed on Oct. 17, 2017, which is a continuation of U.S. patent application Ser. No. 14/563,509, filed on Dec. 8, 2014, now U.S. Pat. No. 9,808,551, granted Nov. 7, 2017, which is a continuation of U.S. patent application Ser. No. 13/111,187, filed on May 19, 2011, now U.S. Pat. No. 8,921,640, granted Dec. 30, 2014, which claims the benefit, under 35 USC § 119(e), of U.S. Provisional Patent Application Ser. Nos. 61/391,353 and 61/391,251, both filed on Oct. 8, 2010, the entire disclosures of which are fully incorporated by reference herein.

FIELD OF INVENTION

The present application relates to absorbent articles, including catamenial devices, such as tampons and sanitary napkins, for the absorption of menses. More particularly, the present invention relates to catamenial devices comprising a lotion composition comprising a rheology structurant and surface energy modifiers, wherein the lotion composition is applied to an outer surface of the device.

BACKGROUND OF THE INVENTION

Disposable absorbent articles, such as diapers, training pants, and catamenial devices, having lotioned topsheets are known. Lotions of different types are known to provide various skin benefits, such as prevention or treatment of skin rash. These lotions can be applied to the topsheet of absorbent articles, for example, and can be transferred to the skin of the wearer during use.

Unlike many types of disposable absorbent articles, catamenial devices, such as pads and pantiliners, are specifically designed to acquire menstrual fluid. Menstrual fluid differs from other exudates, such as urine, in many important properties, such as viscosity, solids, chemical constituents, and/or color content. Therefore, catamenial devices differ from other absorbent articles, like baby diapers, in their structural components to optimize the absorption of menstrual fluid.

Treatments to the bodyside surface of the topsheet of absorbent products provide skin health benefits and allow a fluid, such as urine or menses, to be absorbed into the absorbent product. Skin health benefits may include a reduced direct contamination by body fluids in contact with the body surface and/or delivery of ingredients to improve skin function, i.e., skin barrier. Nonetheless, these treatments are known to impede the acquisition of body fluids and strategies have been designed to position these treatments on regions of the bodyside surface of the topsheet to minimize their effect on fluid acquisition.

Treatments of the bodyside surface of the topsheet of feminine hygiene products also have been proposed to provide skin health benefits, and similarly treatment deployment generally is performed to minimize the hindrance of menstrual fluid acquisition. Nonetheless, topsheet treatments often become ineffective after repeated assaults of body fluids due to deposition of blood cells or other soils on the topsheet surface. In addition, the treatment sometimes provokes negative product failure signals to the user of feminine hygiene product, including the appearance of a dirty or soiled topsheet and/or negative odors. This type of treatment on a topsheet may provide a compromised skin health benefit and an unacceptable appearance of a used feminine hygiene product.

It would be beneficial therefore to provide a treatment for feminine hygiene articles that facilitates migration of menstrual fluid away from the body and through the topsheet into the absorbent core of the article.

Additionally, it would be beneficial to provide a treatment for feminine hygiene articles that enables migration of a fluid, such as menstrual fluid, in a controlled fashion.

Further, it would be beneficial to provide a treatment for feminine hygiene articles that facilitates a fluid, such as menstrual fluid, being moved in a manner that enhances the perceived cleanliness of both the topsheet and the skin of the wearer, especially after multiple assaults of a body fluid.

It also would be beneficial to provide a treatment for feminine hygiene articles that resists fouling of the topsheet and the skin of the wearer of the articles by proteins, lipids, and carbohydrates present in menses.

SUMMARY OF THE INVENTION

A lotion composition is provided. The lotion composition can comprise a) about 1% to about 90%, by weight, of a rheology structurant; and b) a carrier.

Also provided is a lotion composition comprising a) about 1% to about 90%, by weight, of a rheology structurant selected from the group consisting of bayberry wax, ceresin, purcelline, Japan wax, lanolin wax, mink wax, spent grain wax, spermaceti wax, ceresine wax, orange wax, lemon wax, wool wax, ceresin wax, and combinations thereof; and b) a carrier.

Also provided is a lotion composition comprising a) about 1% to about 90%, by weight, of a rheology structurant selected from the group consisting of bayberry wax, ceresin, purcelline, Japan wax, lanolin wax, mink wax, spent grain wax, spermaceti wax, ceresine wax, orange wax, lemon wax, wool wax, ceresin wax, and combinations thereof; and b) a carrier selected from the group consisting of avocado oil, apricot oil, apricot kernel oil, babassu oil, borage oil, borage seed oil, calendula oil, camellia oil, canola oil, carrot oil, cashew nut oil, castor oil, chamomile oil, cherry pit oil, chia oil, coconut oil, cod liver oil, corn oil, corn germ oil, cottonseed oil, eucalyptus oil, evening primrose oil, grape seed oil, hazelnut oil, jojoba oil, juniper oil, kernel oil, linseed oil, macadamia oil, meadowfoam seed oil, menhaden oil, mink oil, moringa oil, mortierella oil, olive oil, palm oil, palm kernel oil, peanut oil, peach kernel oil, rapeseed oil, rose hip oil, safflower oil, sandlewood oil, sesame oil, soybean oil, sunflower oil, sunflower seed oil, sweet almond oil, tall oil, tea tree oil, turnip seed oil, walnut oil, wheat germ oil, zadoary oil, soya oil, turnip seed oil, palm oil, olive oil, sesame oil, cocoa butter, shea butter, or combinations thereof.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The present invention is directed to lotion compositions and to absorbent articles, particularly disposable absorbent articles, having a lotion treatment composition applied thereon. Disposable absorbent articles can be baby diapers or feminine hygiene articles, including incontinence devices and catamenial products, such as tampons, sanitary napkins, pantiliners, interlabial products, and the like. For convenience, the invention is disclosed below with respect to the embodiment of a catamenial device, such as a sanitary napkin or pantiliner.

Figure 1:
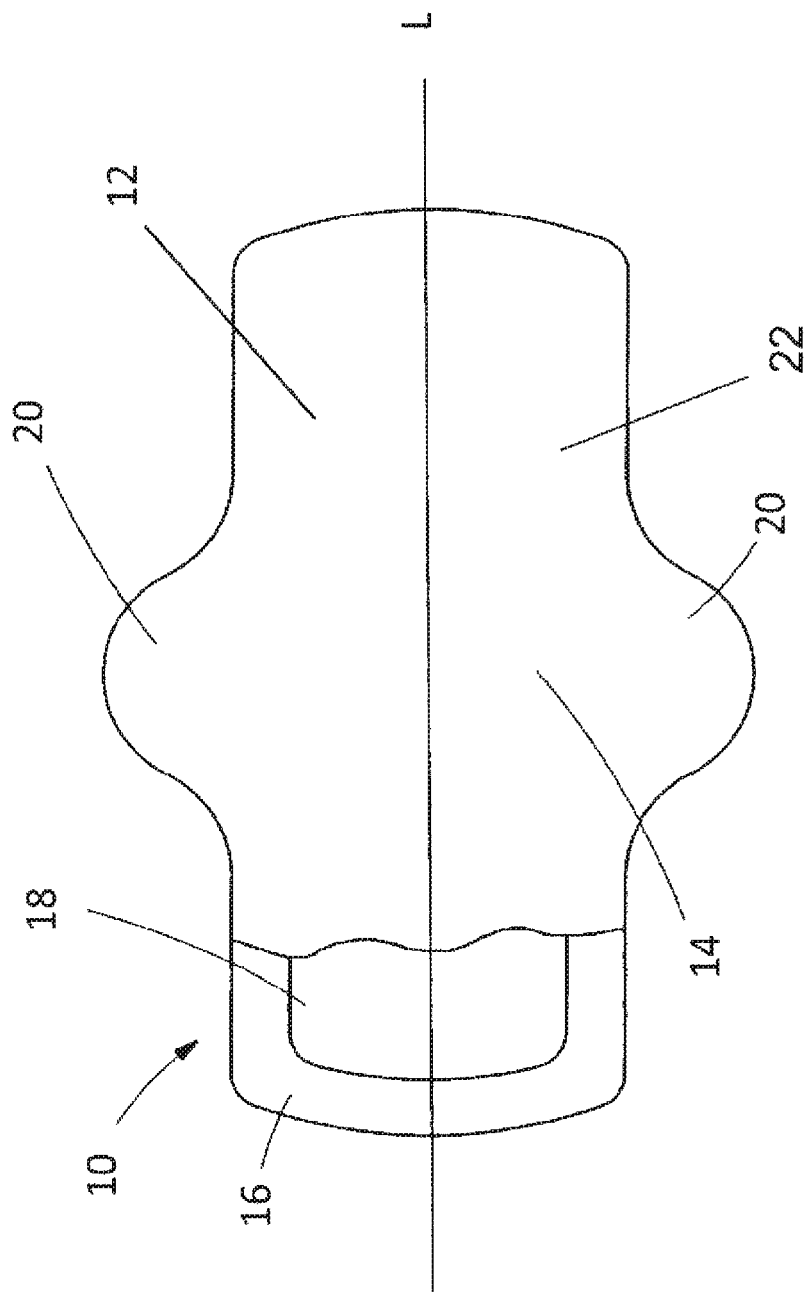
FIG. 1 is a top view of a representative catamenial device.

FIG. 1 shows a sanitary napkin 10, e.g., having a body-contacting surface 12 comprising an outer surface of a topsheet 14, a liquid impervious backsheet 16 joined to the topsheet 14, and an absorbent core 18. The sanitary napkin 10 has a longitudinal axis L and also may be provided with additional features commonly found in napkins, including "wings" or "flaps" 20 as is known in the art, and/or a secondary topsheet, and/or a fluid acquisition layer, and/or other layers designed to promote fluid transport to absorbent core 18. Likewise, topsheet 14 of the sanitary napkin can have various optional characteristics, as is known in the art. For example, topsheet 14 can have one or more of channels embossed therein to direct fluid flow, apertures therethrough to aid in fluid acquisition, and printed signals visible on or through, the visible signals being printed on the topsheet or underlying layers for functional and esthetic properties. Sanitary napkin 10 has a lotion composition applied thereto.

The absorbent article can comprise any known or otherwise effective topsheet, such as one which is compliant, soft feeling, and non-irritating to the body of the wearer. Suitable topsheet materials include a liquid pervious material that is oriented towards and contacts the body of the wearer, thereby permitting body discharges to rapidly penetrate through the topsheet without allowing fluid to flow back through the topsheet to the skin of the wearer. The topsheet, while capable of allowing rapid transfer of fluid through it, also provides for the transfer or migration of the lotion composition onto an external or internal portion of a body of the wearer. A suitable topsheet can be made of various materials, such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof, as is well known in the art of making catamenial products such as sanitary napkins, pantiliners, incontinence pads, and the like.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The absorbent article topsheet can be any suitable topsheet, such as, for example, as described in U.S. Pat. Nos. 4,629,643; 7,172,801; 7,270,861; 7,410,683; 7,507,459; 7,521,588; 7,553,532; 7,648,752; 7,670,665; 7,718,243; 7,732,657; and 7,785,690.

A catamenial device of the present invention can also comprise a backsheet. The backsheet can be any known or otherwise effective backsheet material, provided that the backsheet prevents external leakage of exudates absorbed and contained in the catamenial device. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making catamenial products, such as sanitary napkins, pantiliners, incontinence pads, and the like.

The catamenial device also comprises an absorbent core. The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid absorbent material known in the art for use in absorbent articles, provided that the liquid absorbent material can be configured or constructed to meet absorbent capacity requirements. Nonlimiting examples of liquid absorbent materials suitable for use as the absorbent core include comminuted wood pulp, which is generally referred to as airfelt; creped cellulose wadding; absorbent gelling materials including superabsorbent polymers, such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making catamenial products such as sanitary napkins, pantiliners, incontinence pads, and the like.

A catamenial device of the present invention comprises a lotion composition 22, wherein the lotion composition comprises a rheology structurant and a surface energy modifier. Lotion composition 22 can be applied in any known manner, in any known pattern, and to topsheet 14, including, for example, to the outer surface (i.e., body facing surface) of topsheet 14, such as, for example, as set forth in U.S. Pat. Nos. 6,426,444 and 7,626,073; and U.S. Patent Appln. Nos. 2005/0137544 and 2006/0135920. For example, in certain embodiments, the lotion composition can be applied to an entire surface of the absorbent article, such as the topsheet, or to portions thereof, either uniformly or non-uniformly, such as in patches, swirls, stripes, bands, or along the outer edges, or any combination thereof.

By "non-uniform" it is meant that the amount, location, pattern of distribution, etc. of the lotion composition can vary over the topsheet surface. For example, some portions of the treated surface of the topsheet can have greater or lesser amounts of lotion composition, including portions of the surface that do not have any lotion composition on it. In certain embodiments, the surface of the topsheet will have regions where no lotion is applied, particularly in areas of the topsheet that correspond to the crotch region of the article. In those embodiments where the topsheet comprises discrete, untreated regions, the percent open area of the region of the topsheet that corresponds to the crotch region of the article can be any suitable size.

Where the lotion is applied nonuniformly, any lotion pattern may be utilized, including, for example, application of small droplets (obtained via, e.g., spraying) discrete dots (obtained via, e.g., gravure printing), stripes that run in the longitudinal or lateral direction of the article, etc. In addition, or alternatively, the lotion composition can be disposed near channels or embossed areas when present in the absorbent article. With respect to applying the lotion composition to the outer surface (i.e., body facing surface) of the topsheet, it is believed that the lotion composition helps reduce the adherence of solid components of body fluids, such as menses, to the outer surface of the topsheet, thereby resulting in less staining on the topsheet of the absorbent article. Applying the lotion to the topsheet also enables transfer of a portion of the lotion to the skin of the wearer, resulting in less fouling of the skin of the wearer. The lotion composition as applied to the outer surface of the topsheet also can help to provide a more efficient acquisition of body fluids into the absorbent article.

The lotion composition can be applied at varying add-on levels, depending on the desired fluid handling properties and desired treatment of the skin of the wearer. For example, in certain embodiments involving catamenial devices, the amount of lotion can be variable, and can be tailored for specific needs. For example, while not being bound by theory, it is believed that lotion can be added on at levels of about 0.01 grams per square meter ("gsm"), about 0.05 gsm, about 0.1 gsm, about 0.5, about 1 gsm, about 2 gsm, about 3 gsm, about 4 gsm, about 5 gsm, about 10 gsm, about 25 gsm, about 50 gsm, or about 100 gsm. The lotion can be applied within a range defined by any of the levels recited above (e.g., from about 0.01 gsm to about 100 gsm). These levels refer to the area of the surface actually covered by lotion. In certain embodiments, the minimum level of the lotion composition to be applied to a component of the catamenial device can be an amount effective for reducing the adherence of menses to that component.

Lotion composition 22 of the present invention offers significant advantages over known lotions. The advantage is particularly important for catamenial articles for absorbing menses. Without being bound by any theory, it is believed that the superior fluid handling properties of the lotion disclosed herein is due to how the lotion acts on the solid components of menses, as opposed to surface energy treatments which act on the water component of menses. Known surface energy treatments can be less effective due to the presence of polar and dispersive components in menses, which complicate the effectiveness of surface energy treatments. Furthermore, the surface energy of the treated surfaces can often shift dramatically after the first contact with menses if the treatment composition contains components that induce the solid components of menses to adhere and orient on its surface to reach lower free energy. Because the lotions disclosed herein are not readily soluble in menses, they can effectively coat surfaces without dissolving in menses after repeated insults to provide a hydrated barrier, and because they resist the adhesion of solid components of body fluids, thereby render the menses less prone to fouling surfaces of the disposable absorbent article and the skin of the wearer. Less fouling of the skin of the wearer and/or the topsheet results in better and faster fluid movement, and less visible stain patterns on used products.

In one embodiment, topsheet 14 can be hydrophilic or rendered hydrophilic, and the lotion can be hydrophilic. The levels of hydrophilicity or hydrophobicity can be determined by standard techniques, such as measuring angles that a drop of water make on a surface of material at equilibrium. In general, for the purposes of this invention, a material is considered hydrophilic when a drop of water exhibits an angle of about 60 degrees or less. Fibers are considered hydrophilic when film sheets formed from the polymers of the fibers exhibit contact angles with water less than 60 degrees, more less than 75 degrees, and less than about 90 degrees. Contact angles as a measure of hydrophilicity are well known in the art, and methods for measuring contact angles are equally well known. As also is well known, contact angles greater than about 90 degrees are considered hydrophobic.

A lotion composition of the present invention comprises at least one rheology structurant, which typically is a solid. The lotion composition can further comprise other optional ingredients, like surface energy modifiers.

A "rheology structurant" is a material that helps immobilize lotion ingredients on the topsheet and impede migration through the topsheet into the absorbent core. If the lotion migrates to the absorbent core, the absorption properties of the core decrease, and more lotion must be applied to the topsheet in order to obtain a beneficial effect. The rheology structurant can also assist in transfer of a portion of the lotion to the skin and delivers target sensory at wearing. Typically, a rheology structurant rapidly solidifies on the topsheet after application of the lotion.

The rheology structurant can be provided in an amount of about 0.1% to 90%, by weight of the lotion composition. In a preferred embodiment, the lotion compositions comprise about 1% to about 50% of a rheology structurant, by weight of the lotion composition. In a more preferred embodiment, lotion compositions comprise about 3% to about 30%, of a rheology structurant, by weight of the lotion composition.

A preferred rheology structurant used in a present lotion composition comprises microcrystalline wax.

In addition to a rheology structurant, in certain embodiments, the lotion composition comprises surface energy modifiers. One suitable surface energy modifier is POE-4 monolaurate, i.e., a polyoxyethylene ester of lauric acid, wherein the polyoxyethylene moiety contains an average of four ethylene oxide units. POE-4 monolaurate has a structure

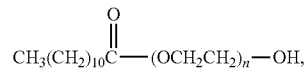

wherein n has an average value of 4.

In certain embodiments, the POE-4 monolaurate can be present in the lotion in an amount of 0.1% to about 25%, and preferably about 1% to about 20%, by weight, of the lotion. More preferably, the POE-4 monolaurate is present in an amount of about 2% to about 12%, by weight, of the lotion composition.

In certain embodiments, the lotion composition can also comprise POE-8 monostearate as a second surface energy modifier. POE-8 monostearate is a polyoxyethylene ester of stearic acid containing an average of eight ethylene oxide units, and having a structure

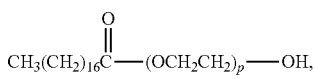

wherein p has an average value of 8.

The POE-8 monostearate can be present in the lotion in an amount of about 0.1% to about 50%, and preferably about 1% to about 30%, by weight, of the lotion. More preferably, the POE-8 monostearate is present in an amount of about 3% to about 15%, by weight, of the lotion composition.

Without being bound by any theory, it is thought that the combination of POE-4 monolaurate and POE-8 monostearate can provide a rapid transfer of a relatively mobile portion of the lotion to the skin of the wearer resulting in a film on the skin that resists dissolving in menses and protects the skin from fouling. The combination of POE-4 monolaurate and POE-8 monostearate with rheology structurant such as microcrystalline wax can also provide a relatively immobile portion of the lotion that remains on the topsheet to facilitate migration of the menses through the topsheet and absorption of the menses by the absorbent core, which helps prevent fouling of the top sheet by the menses for the entire time the absorbent article is used by the wearer.

In addition to the rheology structurant and surface energy modifiers, lotion compositions of the present invention optionally can further comprise one or more body treatment agents, for example hexamidine, zinc oxide, and niacinamide, which are highly effective in the prevention and treatment of erythema, malodor, and bacterial skin disorders, especially when a lotion composition is administered to the body from application on absorbent articles. Additional body treatment agents are disclosed in U.S. Patent Publication No. 2005/0129651.

Lotions compositions of the present invention also can include additional optional components known to persons skilled in the art of lotions for catamenial devices. One such optional ingredient is a fumed silica to adjust lotion viscosity and thickness to a desired level. Additional viscosity and thickening agents are disclosed in U.S. Patent Publication No. 2005/0129651. Other optional ingredients include glycerin, chamomile, skin conditioners, perfumes, deodorants, preservatives, astringents, opacifiers, proteins, urea, lecithin, fats, oils, essential oils, pH control agents, and antibacterials, each in an amount to perform its intended function without adversely affecting the lotion composition, e.g., about 0.001% to about 5% by weight of the lotion composition.

Lotion compositions of the present invention further comprise a carrier. The carrier can be an individual carrier or a blend two or more of carriers, provided that the total carrier concentration is sufficient to provide transfer and/or migration of the rheology structurant, surface energy modifiers, and/or optional body treatment agents onto the body and to promote fluid acquisition into the absorbent article without causing fouling issues. The carrier can be a liquid, solid, or semisolid carrier material, or a mixture of these materials, provided that the resultant carrier forms a homogenous mixture, solution, stable emulsion, or stable dispersion at selected processing temperatures for the resultant carrier system and at processing temperatures for combining the carrier system with the skin treatment agents, surface energy modifiers and rheology structurants in formulating the lotion compositions herein. The preferred carrier system would enable the finished lotion to be semi-solid or solid at ambient, liquid or semi-solid at body temperature and liquid with processible viscosity at 60-90 C.

The lotion compositions of the present invention comprise a carrier in an amount of about 5% to about 95%, preferably about 10% to about 85%, more preferably from about 30% to about 80%, by weight of the lotion composition. Suitable carrier compounds include petroleum-based hydrocarbons having from about 8 to about 32 carbon atoms, fatty alcohols having from about 12 to about 18 carbon atoms, polysiloxane compounds, fatty acid esters, alkyl ethoxylates, lower alcohols having from about 2 to about 6 carbon atoms, low molecular weight glycols and polyols, fatty alcohol ethers having from about 12 to about 22 carbon atoms in their fatty chain, lanolin and its derivatives, ethylene glycol derivatives of $C_{12}$-$C_{22}$ fatty acids, glyceride and its derivatives including acetoglycerides and ethoxylated glycerides of $C_{12}$-$C_{18}$ fatty acids, and mixtures thereof. Alternatively or in combination with, the carrier also may comprise polysiloxane compounds non-limiting examples include $C_{12}$-$C_{28}$ alkyl dimethicones, $C_{12}$-$C_{28}$ alkyl methicones, alkylated silicones (hair conditioning agents), silicone waxes, copolymers of silicone (vinyl dimethicone polymers, phenyl vinyl dimethicone polymers, alkylated silicone polymers, polyethylene oxide/silicone copolymers, polyethylene oxide/polypropolene oxide/silicone copolymers, polypropylene oxide/silicone copolymers, polyethylene oxide/alkyl silicone copolymers, polyethylene oxide/propylene oxide/alkyl silicone copolymers, polypropylene oxide/alkyl silicone copolymers), and mixtures thereof.

Nonlimiting examples of suitable petroleum-based hydrocarbons having from about 8 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to semicrystalline mixtures of hydrocarbons having from about 16 to about 32 carbon atoms. An example of commercially available petrolatum include petrolatum sold as white PROTOPET®-1S, available from the Sonneborn Corporation.

Other suitable carriers include oils or fats, such as natural oils or fats, or natural oil or fat derivatives, in particular of plant or animal origin. Non-limiting examples include avocado oil, apricot oil, apricot kernel oil, babassu oil, borage oil, borage seed oil, calendula oil, camellia oil, canola oil, carrot oil, cashew nut oil, castor oil, chamomile oil, cherry pit oil, chia oil, coconut oil, cod liver oil, corn oil, corn germ oil, cottonseed oil, eucalyptus oil, evening primrose oil, grape seed oil, hazelnut oil, jojoba oil, juniper oil, kernel oil, linseed oil, macadamia oil, meadowfoam seed oil, menhaden oil, mink oil, moringa oil, mortierella oil, olive oil, palm oil, palm kernel oil, peanut oil, peach kernel oil, rapeseed oil, rose hip oil, safflower oil, sandlewood oil, sesame oil, soybean oil, sunflower oil, sunflower seed oil, sweet almond oil, tall oil, tea tree oil, turnip seed oil, walnut oil, wheat germ oil, zadoary oil, or the hardened derivatives thereof. Hardened oils or fats from vegetal origin can include, e.g. hardened castor oil, peanut oil, soya oil, turnip seed oil, cottonseed oil, sunflower oil, palm oil, kernel oil, linseed oil, corn oil, olive oil, sesame oil, cocoa butter, shea butter, and coconut oil.

Other non-limiting examples of fats and oils include: butter, $C_{12}$-$C_{18}$ fatty acid triglyceride, camellia oil, caprylic/capric/lauric triglyceride, caprylic/capric/linoleic triglyceride, caprylic/capric/stearic triglyceride, caprylic/capric triglyceride, cocoa butter, egg oil, epoxidized soybean oil, glyceryl triacetyl hydroxystearate, glyceryl triacetyl ricinoleate, glycosphingolipids, human placental lipids, hybrid safflower oil, hybrid sunflower seed oil, hydrogenated castor oil, hydrogenated castor oil laurate, hydrogenated coconut oil, hydrogenated cottonseed oil, hydrogenated $C_{12}$-$C_{18}$ triglycerides, hydrogenated fish oil, hydrogenated lard, hydrogenated menhaden oil, hydrogenated mink oil, hydrogenated orange roughy oil, hydrogenated palm kernel oil, hydrogenated palm oil, hydrogenated peanut oil, hydrogenated shark liver oil, hydrogenated soybean oil, hydrogenated tallow, hydrogenated vegetable oil, lanolin and lanolin derivatives, lanolin alcohol, lard, lauric/palmitic/oleic triglyceride, lesquerella oil, maleated soybean oil, meadowfoam oil, neatsfoot oil, oleic/linoleic triglyceride, oleic/palmitic/lauric/myristic/linoleic triglyceride, oleostearine, olive husk oil, omental lipids, orange roughy oil, pengawar djambi oil, pentadesma butter, phospholipids, pistachio nut oil, placental lipids, rapeseed oil, rice bran oil, shark liver oil, shea butter, sphingolipids, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, vegetable oil, wheat bran lipids, and the like, as well as mixtures thereof.

Other suitable carriers include mono- or di-glycerides, such as those derived from saturated or unsaturated, linear or branch chained, substituted or unsubstituted fatty acids or fatty acid mixtures. Examples of mono- or diglycerides include mono- or di-$C_{12-18}$ fatty acid glycerides, specifically mono- or di-$C_{14-18}$ fatty acid glycerides, for example glyceryl monomyristate, glyceryl dimyristate, glyceryl monopalmitate and glyceryl dipalmitate.

Carriers can also include esters of linear or branched, saturated or unsaturated $C_6$-$C_{22}$-fatty acids with diol or polyols. Non-limiting examples include ethylene glycol monomyristate, ethylene glycol dimyristate, ethylene glycol palmitate, ethylene glycol dipalmitate, ethylene glycol di(hydroxylstearate), glyceryl dimyristate, glyceryl trimyristate, glyceryl dipalmitate, glyceryl tripalmitate, glyceryl tri(hydroxystearate), sorbitan monomyristate, sorbitan dimyristate, sorbitan trimyristate, sorbitan monooleate, sorbitan dioleate, sorbitan trioleate, sorbitan monoricinoleate, sorbitan diricinoleate, sorbitan triricinoleate, sorbitan di(hydroxystearate), sorbitan tri(hydroxystearate), sucrose monomyristate, sucrose dimyristate, sucrose trimyristate, sucrose tetramyristate, sucrose monopalmitate, sucrose dipalmitate, sucrose tripalmitate, sucrose tetrapalmitate, sucrose tetraoleate, pentaerythrityl dimyristate, pentaerythrityl trimyristate, pentaerythrityl tetramyristate, pentaerythrityl dipalmitate, pentaerythrityl tripalmitate, pentaerythrityl tetrapalmitate, as well as mixtures thereof.

The carrier of the present invention can also include sterols, phytosterols, and sterol derivatives. Sterols and sterol derivatives that can be used in the lotion compositions of the invention include, but are not limited to: β-sterols having a tail on the 17 position and having no polar groups for example, cholesterol, sitosterol, stigmasterol, and ergosterol, as well as, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, "AVOCADIN" (trade name of Croda Ltd of Parsippany, N.J.), sterol esters and similar compounds, as well as mixtures thereof. A commercially available example of phytosterol is GENEROL 122 N PRL refined soy sterol from Cognis Corporation of Cincinnati, Ohio.

Nonlimiting examples of suitable fatty alcohols having from about 12 to about 18 carbon atoms include saturated, unsubstituted, monohydric alcohols or combinations thereof, which have a melting point less than about 110° C., preferably from about 45° C. to about 90° C. Specific examples of fatty alcohol carriers for use in the lotion compositions of the present invention include, but are not limited to, cetyl alcohol, stearyl alcohol, cetearyl alcohol, and combinations thereof. Examples of commercially available cetearyl alcohol is STENOL 1822, which is available from the Cognis Corporation, Cincinnati, Ohio.

Nonlimiting examples of suitable fatty acid esters include those fatty acid esters derived from a mixture of saturated ($C_{12}$-$C_{28}$ preferably $C_{16}$-$C_{24}$) fatty acids and short chain ($C_1$-$C_8$, preferably $C_1$-$C_3$) monohydric alcohols, a mixture of $C_{12}$-$C_{22}$ hydroxyfatty acid and short chain ($C_1$-$C_8$, preferably $C_1$-$C_3$) monohydric alcohols, a mixture of saturated ($C_{12}$-$C_{28}$ preferably $C_{16}$-$C_{24}$) fatty acids and unsaturated ($C_3$-$C_{18}$ preferably $C_8$-$C_{18}$) monohydric alcohols, or a mixture of $C_{12}$-$C_{22}$ hydroxyfatty acids and unsaturated ($C_3$-$C_{18}$ preferably $C_8$-$C_{18}$) monohydric alcohols. Suitable fatty acid esters can also be derived from esters of longer chain saturated ($C_{12}$-$C_{28}$, preferably $C_{14}$-$C_{22}$) fatty alcohols and shorter chain fatty acids such as lactic acid, or from esters of longer chain saturated fatty alcohols ($C_{12}$-$C_{28}$, preferably $C_{14}$-$C_{22}$) and unsaturated fatty acids such as oleic acid. Representative examples of suitable fatty acid esters include methyl palmitate, methyl stearate, methyl hydroxystearate, methyl isostearate, isopropyl myristate, isopropyl palmitate, isopropyl stearate, isopropyl isostearate, isopropyl hydroxystearate, ethylhexyl myristate, ethylhexyl palmitate, ethylhexyl stearare, ethylhexyl isosterate, ethylhexyl hydroxystearate, stearyl heptanoate, stearyl octanoate, myristyl oleate, myristyl ricinoleate, cetyl oleate, cetyl ricinoleate, stearyl oleate, stearyl ricinoleate, isostearyl oleate, isostearyl ricinoleate, oleyl myristate, oleyl palmitate, oleyl stearate, oleyl isostearate, oleyl behenate, oleyl erucate, behenyl oleate, behenyl ricinoleate, myristyl lactate, cetyl lactate, stearyl lactate, isostearyl lactate and mixtures thereof.

Nonlimiting examples of suitable alkyl ethoxylates or alkyl propoxylates include $C_{12}$-$C_{22}$ fatty alcohol ether ethoxylates having an average degree of ethoxylation of from about 1 to about 20 or $C_{12}$-$C_{22}$ fatty alcohol ether propoxylates having an average degree of propoxylation of from about 1 to about 20. Nonlimiting examples of suitable alkyl ethoxylates and alkyl propoxylates include steareth-1, steareth-2, steareth-3, steareth-4, steareth-6, steareth-8, beheneth-4, beheneth-8, PPG-1 myristyl ether, PPG-2 myristyl ether, PPG-3 myristyl ether, PPG-1 stearyl ether, PPG-2 stearyl ether, PPG-3 stearyl ether, PPG-10 stearyl ether, PPG-15 stearyl ether, PPG-2 behenyl ether, PPG-3 behenyl ether, PPG-4 behenyl ether and PPG-10 behenyl ether. Nonlimiting examples of suitable lower alcohols having from about 2 to about 6 carbon atoms include butanediol, 1,2,4-butanetriol, 1,2 hexanediol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol and mixtures thereof. A more detailed description of carrier ingredients including suitable hydrocarbons, polysiloxane compounds, and fatty alcohol ethoxylates can be found in U.S. Pat. No. 5,643,588, incorporated herein by reference in its entirety.

Suitable carriers further encompass waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Suitable waxes which can be incorporated into the lotion composition include animal, vegetable, mineral or silicone based waxes which may be natural or synthetic, and including mixtures thereof. Waxes can include but are not limited to: natural waxes from vegetal origin, such as bayberry wax, ceresin, purcelline, Japan wax, lanolin wax, mink wax, spent grain wax, spermaceti wax, ceresine wax, fruit-derived waxes, such as orange wax, lemon wax, and bayberry wax, and the like; and waxes from animal origin such as wool wax and the like. Natural waxes further comprise mineral waxes such as ceresin wax. Synthetic waxes comprise petroleum-based waxes, such as certain carrier materials described hereinbefore, such as paraffin, Vaseline, petrolatum, micro wax, and microcrystalline wax. Further suitable synthetic waxes are polyalkylene and polyethyleneglycol waxes, e.g. polyethylene wax; waxes based on chlorinated naphtalenes such as 'Halowax', synthetic hydrocarbon waxes, and the like, PEG-6 beeswax, PEG-8 beeswax, $C_{16-28}$ alkyl dimethicone, synthetic Japan wax, synthetic jojoba wax, including mixtures thereof. Further suitable waxes are chemically modified waxes, in particular hardened or hydrogenated waxes such as, for example, hydrogenated cottonseed oil, hydrogenated jojoba oil, hydrogenated microcrystalline wax, jojoba esters, and the like.

Other wax components can be certain fats (including $C_{12}$-$C_{18}$ mono-, di- and triglycerides), $C_8$-$C_{18}$ dialkyl(ene) ethers, $C_8$-$C_{18}$ dialkyl(ene) carbonates, $C_8$-$C_{18}$ dicarboxylic acids. Further wax components that can be used are tri-$C_8$-$C_{18}$-alkyl citrates, e.g., tristearyl citrate, triisostearyl citrate, trimyristyl citrate, trilauryl citrate; ethyleneglycol di fatty acid esters, in particular the ethylene glycol di-$C_{12}$-$C_{18}$-fatty acid esters, e.g., ethylene glycol dipalmitate, ethylene glycol dimyristate; the glyceryl di- or tri-$C_{12}$-$C_{18}$-fatty acid esters, e.g. glyceryl trimyristate, glyceryl tripalmitate.

Other suitable carriers include materials that act as solidifying agents, including some of the materials described hereinbefore. Suitable solidifying agent(s) in the lotion compositions of the present invention can function to help solidify the composition so that the composition is a solid at room temperature and has a melting point of at least 32° C. The solidifying agent may also provide a tackiness to the composition that improves the transfer by adhesion to the skin of the wearer. Depending on the solidifying agent selected, the solidifying agent can also modify the mode of transfer so that the composition tends to fracture or flake off instead of actually rubbing off onto the skin of the wearer which can lead to improved transfer to the skin. The solidifying agent may further function as an emollient, occlusive agent, moisturizer, barrier enhancer, viscosity enhancer and combinations thereof. The solidifying agents can be selected from microcrystalline wax, alkyl siloxanes, fatty acid esters, alkyl hydroxystearates, branched esters (such as di substituted glycols with fatty acids, di substituted glycols with hydroxystearates, di or tri glycerides, di or tri substituted citrates and di, tri, or tetra substituted pentaerythritol), di substituted ethylene amides, low density polyethylenes, polystyrenes, polyamdies, alkoxylated alcohols and alkoxylated carboxylic acid, with a melting point of 40° C. or greater. Examples of suitable solidifying agents include, but are not limited to, the following: microcrystalline wax, $C_{30}$ alkyl dimethicone, $C_{24}$-$C_{28}$ alkyl dimethicone, cerotyl dimethicone, stearyl dimethicone, cetyl dimethicone, stearyl methicone, cetyl methicone, $C_1$-$C_{18}$ alkyl behenate, $C_{16}$-$C_{24}$ lactate, isopropyl lignocerate, ethylhexyl lignocerate, lauryl lignocerate, myristyl lignocerate, isopropyl behenate, ethylhexyl behenate, lauryl behenate, tridecyl behenate, myristyl behenate, cetyl behenate, isostearyl behenate, ethylhexyl stearate, lauryl stearate, tridecyl stearate, myristyl stearate, cetyl stearate, isostearyl stearate, stearyl stearate, behenyl isostearate, stearyl isostearate, cetyl isostearate, lauryl palmiate, myristyl palmitate, cetyl palmitate, stearyl palmitate, isostearyl palmitate, myristyl myristate, cetyl myristate, isotearyl myristate, stearyl myristate, behehenyl myristate, cetyl laurate, stearyl laurate, isostearyl laurate, behenyl laurate, octyidodecyl stearate; octyidodecyl stearoyl stearate, $C_{14}$-$C_{24}$ alkyl hydroxystearate, stearyl benzoate, isostearyl benzoate, behenyl benzoate, di $C_2$-$C_5$ alkyl fumerate, stearyl lactate, behenyl lactate, ethylene glycol dibehenate ester, ethylene glycol distearate ester, ethylene glycol diisostearate ester, ethylene glycol di(hydroxystearate), glycerol tribehenate ester, glycerol dibehenate ester, glyceryl tristearate ester, glyceryl distearate ester, glyceryl triisostearate ester, glyceryl diisostearate ester, glyceryl tri(hydroxystearate), glyceryl di(hydroxystearate), tribehenyl citrate, dibehenyl citrate, tristearyl citrate, distearyl citrate, triisostearyl citrate, diisostearyl citrate, tricetyl citrate, dicetyl citrate, sorbitan tetrabehenate, sorbitan tribehenate, sorbitan dibehenate, sorbitan tetrasteate, sorbitan tristearate, sorbitan distearate, sorbitan tetraisostearate, sorbitan triisostearate, sorbitan diisostearate, sorbitan tetrapalmitate, sorbitan tripalmitate, sorbitan dipalmitate, sucrose tetrabehenate, sucrose tribehenate, sucrose dibehenate, sucrose, tetrastearate, sucrose tristearate, sucrose distearate, sucrose tetraisostearate, sucrose triisostearate, sucrose diisostearate, sucrose tetrapalmitate, sucrose tripalmitate, sucrose dipalmitate, pentaerythrityl tetrabehenate, pentaerythrityl distearate, pentaerythrityl tetramyristate, pentaerythrityl tetrapalmitate, pentaerythrityl tetrastearate, pentaerythrityl tetraisostearate, pentaerythrityl tetra(hydroxystearate), ethylene bisoleamide, low density polyethylene, polypropylene, polybutene, polyamides, polystyrene, poly(vinyl acetate), glycol montanate, fluoranated waxes, steareth-1, steareth-2, steareth-3, steareth-4, steareth-6, steareth-10, beheneth-1, beheneth-2, beheneth-3 beheneth-4, beheneth-8, ethylene glycol monostearate, POE-2 monostearate, POE-3 monostearate, POE-8 monostearate, propylene glycol monobehenate, ethylene glycol monobehenate, POE-2 monobehenate, POE-3 monobehenate, POE-10 monobehenate, and mixtures of such compounds.

In certain embodiments, the lotion composition can be substantially free of water, meaning that water typically is not intentionally added to the lotion composition. However, small amounts of water may be present in an ingredient of the lotion composition or as a result of humidity. Typically, a present lotion composition comprises less than 5%, preferably less than 1%, and more preferably less than 0.5%, by weight, water.

In preparing a lotioned catamenial device according to the present invention, the lotion composition can be applied to the outer surface of the absorbent article, such as, for example, the outer surface of the topsheet. Any of a variety of application methods that distribute lubricious materials having a molten or liquid consistency can be used, such as, for example, as set forth in U.S. Pat. No. 5,968,025 and U.S. Patent Appln. No. 2005/0208113. Suitable methods include but are not limited to spraying, printing (e.g., flexographic printing), coating (e.g., gravure coating), extrusion, dipping, or combinations of these application techniques, e.g., spraying the lotion composition on a rotating surface, such as a calender roll, that then transfers the composition to the outer surface of the sanitary napkin topsheet. Additionally, the manner of applying the lotion composition to a portion of a catamenial device can be such that the substrate or component does not become saturated with the lotion composition. The lotion composition can be applied to the catamenial device at any point during assembly. For example, the lotion composition can also be applied to the outer surface of the topsheet before it is combined with the other raw materials to form a finished catamenial device.

In certain embodiments, the lotion composition does not have a tendency to migrate to the interior of the topsheet to which it is applied. Therefore, less lotion composition is required to impart the desired coating and anti-fouling benefits. In certain embodiments, however, the lotion composition can be transferable to the skin of the wearer by normal contact, wearer motion, and/or body heat.

Lotions of the present invention facilitate fluid acquisition through the top sheet to the absorbent core of an absorbent article, and resist fouling of the topsheet and the skin of the wearer by the proteins, lipids, and carbohydrates present in menses. Non-limiting example lotion compositions are illustrated in the following Examples 1-4.

Example 1

| Component | Trade Name | Supplier | Weight % |
|---|---|---|---|
| Microcrystalline Wax | MULTIWAX W-835 | Sonneborn | 17 |
| POE-4 Monolaurate | PEGOSPERSE-200ML | Lonza | 8 |
| POE-8 Monostearate | MYRJ-S8-SO | Croda | 10 |
| Zinc Oxide Premix[1)] | Zinc Oxide Premix | Kobo | 7 |
| Fumed Silica | CAB-O-SIL TS-720 | Cabot | 4 |
| Petrolatum | WHITE PROTOPET-1S | Sonneborn | balance |

[1)]Zinc oxide premix contains 69.8% zinc oxide, by weight, dispersed in the mixture of isononyl isononanoate and polyhydroxstearic acid.

Example 2

| Component | Trade Name | Supplier | Weight % |
|---|---|---|---|
| Microcrystalline Wax | MULTIWAX W-835 | Sonneborn | 14 |
| POE-4 Monolaurate | PEGOSPERSE-200ML | Lonza | 6 |
| POE-8 Monostearate | MYRJ-S8-SO | Croda | 7.5 |
| Lauryl Alcohol | CO-1270 | P&G | 3 |
| Zinc Oxide Premix[1)] | Zinc Oxide Premix | Kobo | 7 |
| Fumed Silica | CAB-O-SIL TS-720 | Cabot | 4 |
| Petrolatum | WHITE PROTOPET-1S | Sonneborn | balance |

Example 3

| Component | Trade Name | Supplier | Weight % |
|---|---|---|---|
| Microcrystalline Wax | MULTIWAX W-835 | Sonneborn | 14 |
| POE-4 Monolaurate | PEGOSPERSE-200ML | Lonza | 4 |
| POE-8 Monostearate | MYRJ-S8-SO | Croda | 4.5 |
| Fumed Silica | CAB-O-SIL TS-720 | Cabot | 4 |
| Petrolatum | WHITE PROTOPET-1S | Sonneborn | balance |

Example 4

| Component | Trade Name | Supplier | Weight % |
|---|---|---|---|
| Microcrystalline Wax | MULTIWAX W-835 | Sonneborn | 12 |
| POE-4 Monolaurate | PEGOSPERSE-200ML | Lonza | 4 |
| POE-8 Monostearate | MYRJ-S8-SO | Croda | 4.5 |
| Polypropylene Glycol - 4000 | PLURIOL P-4000 | BASF | 4 |
| Zinc Oxide Premix[1)] | Zinc Oxide Premix | Kobo | 7 |
| Fumed Silica | CAB-O-SIL TS-720 | Cabot | 4 |
| Petrolatum | WHITE PROTOPET-1S | Sonneborn | balance |

Example 5

| Component | Trade Name | Supplier | Weight % |
|---|---|---|---|
| Microcrystalline Wax | MULTIWAX W-835 | Sonneborn | 17 |
| C28 Alkyl Dimethicone | Silwax Di5026 | Siltech | 6 |
| POE-4 Monolaurate | PEGOSPERSE-200ML | Lonza | 7.5 |
| POE-8 Monostearate | MYRJ-S8-SO | Croda | 6 |
| Zinc Oxide Premix[1)] | Zinc Oxide Premix | Kobo | 7 |
| Fumed Silica | CAB-O-SIL TS-720 | Cabot | 4 |
| Petrolatum | WHITE PROTOPET-1S | Sonneborn | balance |

Example 6

| Component | Trade Name | Supplier | Weight % |
|---|---|---|---|
| Microcrystalline Wax | MULTIWAX W-835 | Sonneborn | 12 |
| C30 Alkyl Dimethicone | Silwax C41M90 | Clariant | 1 |
| C28 Alkyl Dimethicone | Silwax Di5026 | Siltech | 6 |
| POE-4 Monolaurate | PEGOSPERSE-200ML | Lonza | 10 |
| POE-8 Monostearate | MYRJ-S8-SO | Croda | 15 |

-continued

| Component | Trade Name | Supplier | Weight % |
|---|---|---|---|
| Zinc Oxide Premix[1)] | Zinc Oxide Premix | Kobo | 7 |
| Fumed Silica | CAB-O-SIL TS-720 | Cabot | 4 |
| Petrolatum | WHITE PROTOPET-1S | Sonneborn | balance |

Example 7

Example 5 demonstrates that FT-IR measurements of lotion surface fouling show that the lotions of Example 1 results in less surface adsorption of protein, carbohydrates, and lipids from a synthetic menstrual fluid as compared to Known Lotion A and Known Lotion B.

| INGREDIENTS | (wt %): |
|---|---|
| Known Lotion A: | |
| Lanette 22 (Behenyl Alcohol) | 8.92 |
| Chamomile, phytoconcentrol oil | 0.5 |
| Petrolatum | 80.28 |
| Silicon Dioxide, treated | 3.2 |
| Zinc Oxide Dispersion (71% ZnO) | 7.1 |
| Known Lotion B: | |
| Beheneth-10 | 10 |
| Lanette 22 (Behenyl Alcohol) | 5.0 |
| Petrolatum | 68.4 |
| Silicon Dioxide, treated | 3.5 |
| Zinc Oxide Dispersion (71% ZnO) | 7.1 |
| PPG 4000 (Pluriol P4000) | 6 |

A germanium internal reflection element was dipped into a 0.1% lotion in hexanes solution, air dried, and inserted into a standard-sized flow-through Spectra-Tech cylindrical attenuated total reflection cell (CIRCLE™ cell). The cell was filled with water and a reference spectrum collected. The FT-IR was set up to collect a spectrum every 0.3 of a second and 40 milliliters of synthetic menstrual fluid was injected into the water-filled cell using a syringe pump. Data collection was stopped approximately 5 minutes after the injection of synthetic menstrual fluid. FT-IR measurements were taken as set forth in Story, G. M. and Marcott, C., "Monitoring Enzyme Adsorption on Model Substrates Using Infrared Attenuated Total Reflectance Spectroscopy." Proceedings of the 7th International Conference on Fourier Transform Spectroscopy, SPIE, 1145, 145 (1989); and Story, G. M., Rauch, D. S., Brode III, P. F., and Marcott C.: "Infrared Analysis of Enzymes Adsorbed onto Model Surfaces,", ACS Symposium Series No. 447, Fourier Transform Infrared Spectroscopy in Colloid and Interface Science, D. R. Scheuing, Ed., American Chemical Society, 225, 1991.

Figure 2A:
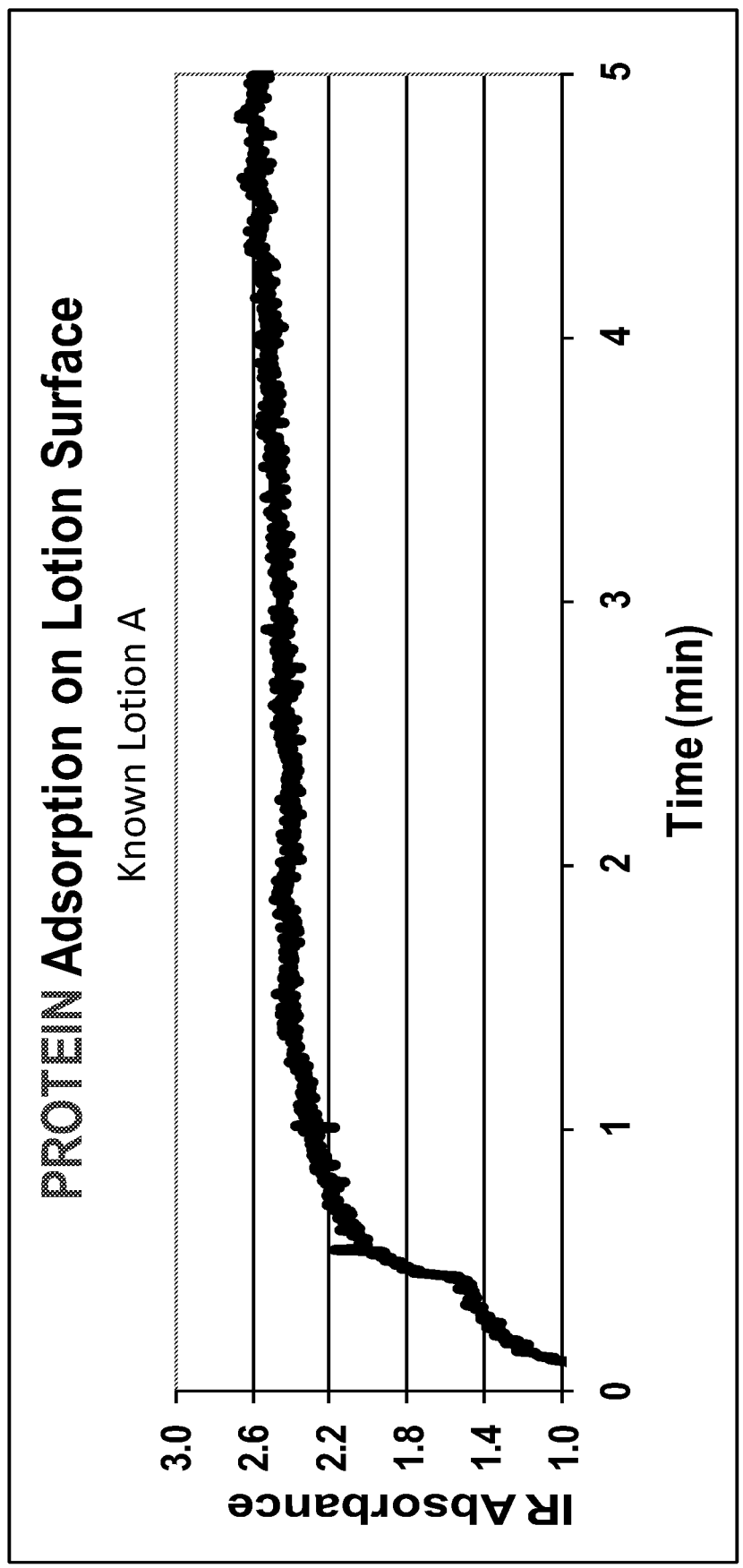
FIGS. 2a, b, and c show a plot of IR absorbance vs. time showing the reduced protein fouling achieved by a present lotion composition or a commercially used lotion.
Figure 2B:
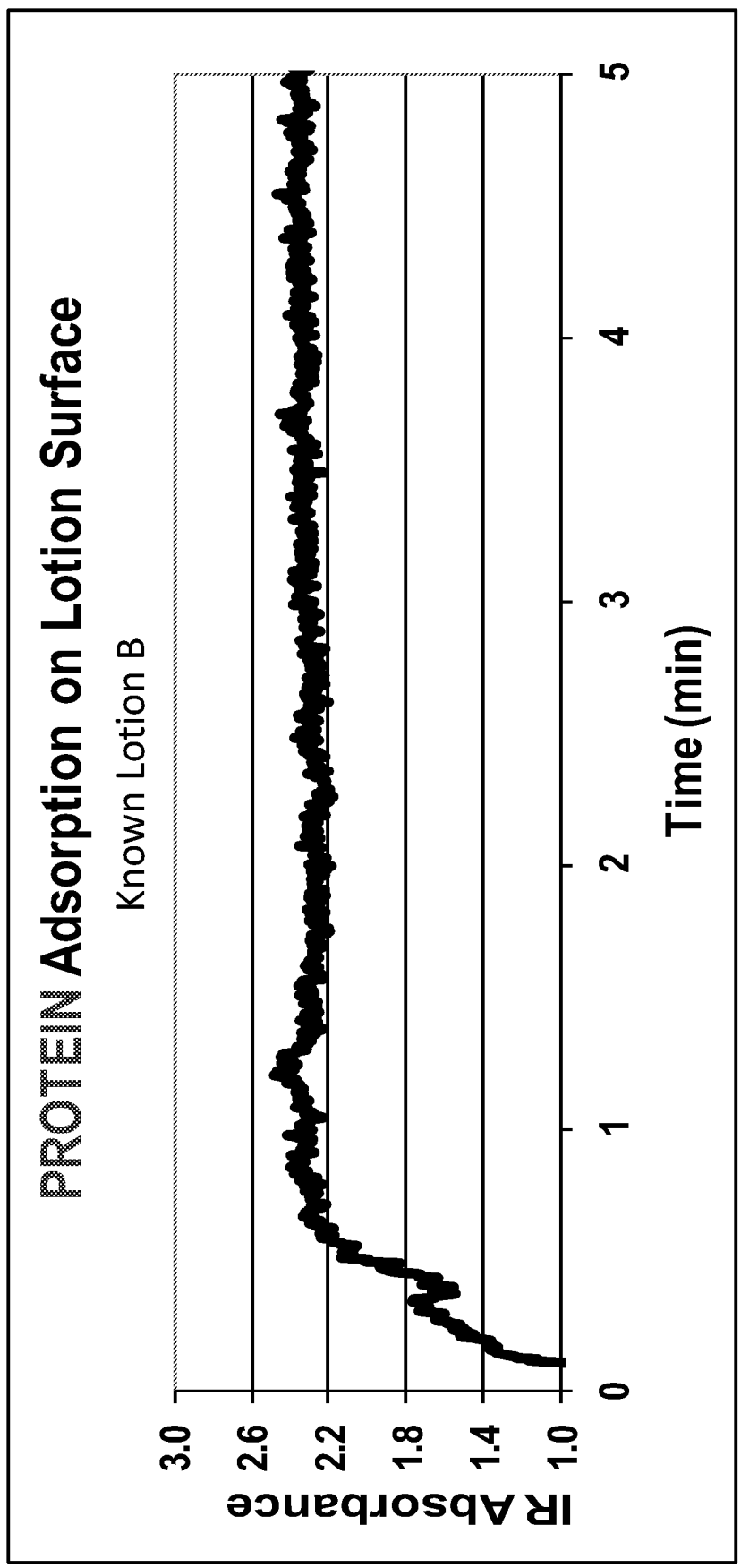
Figure 2C:
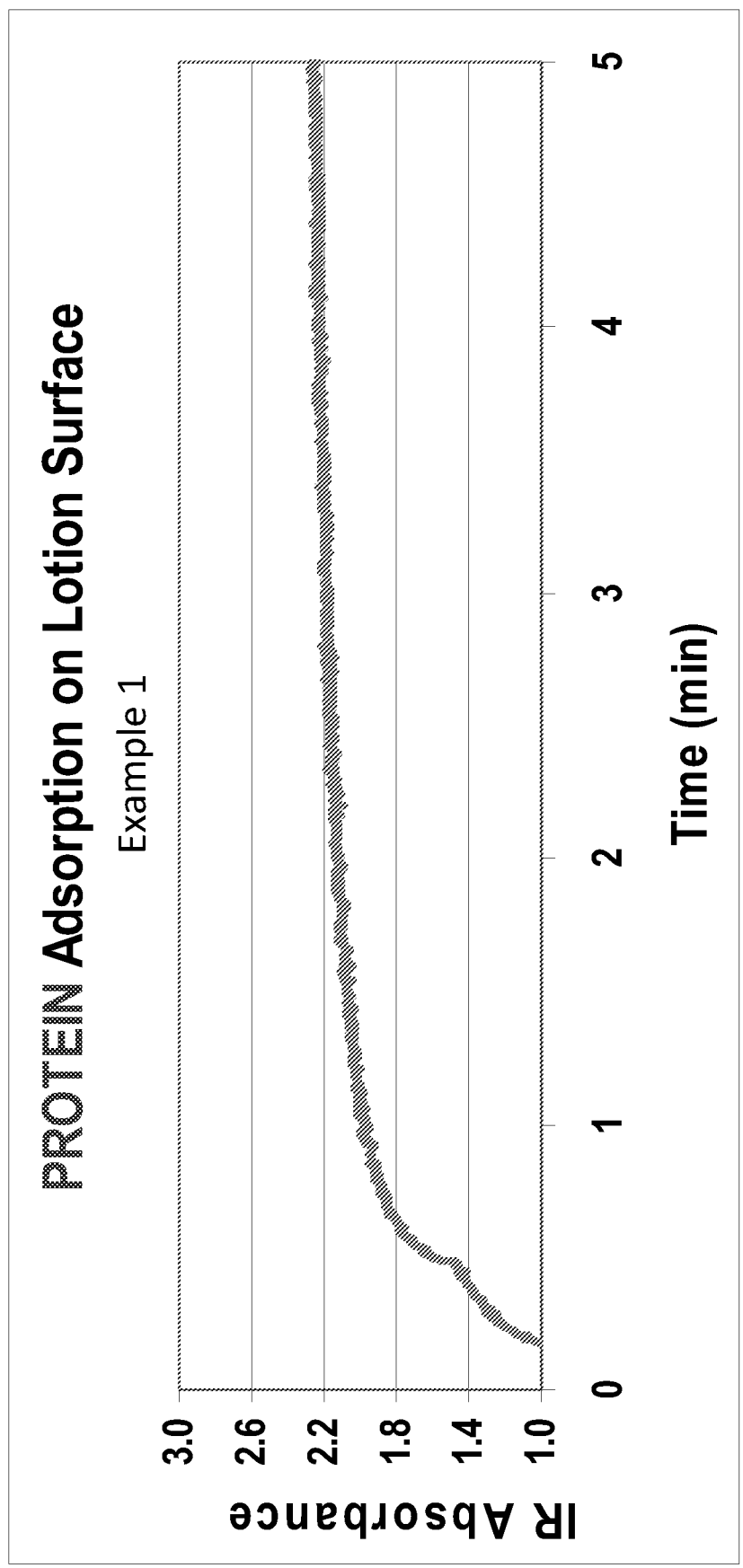
Figure 3A:
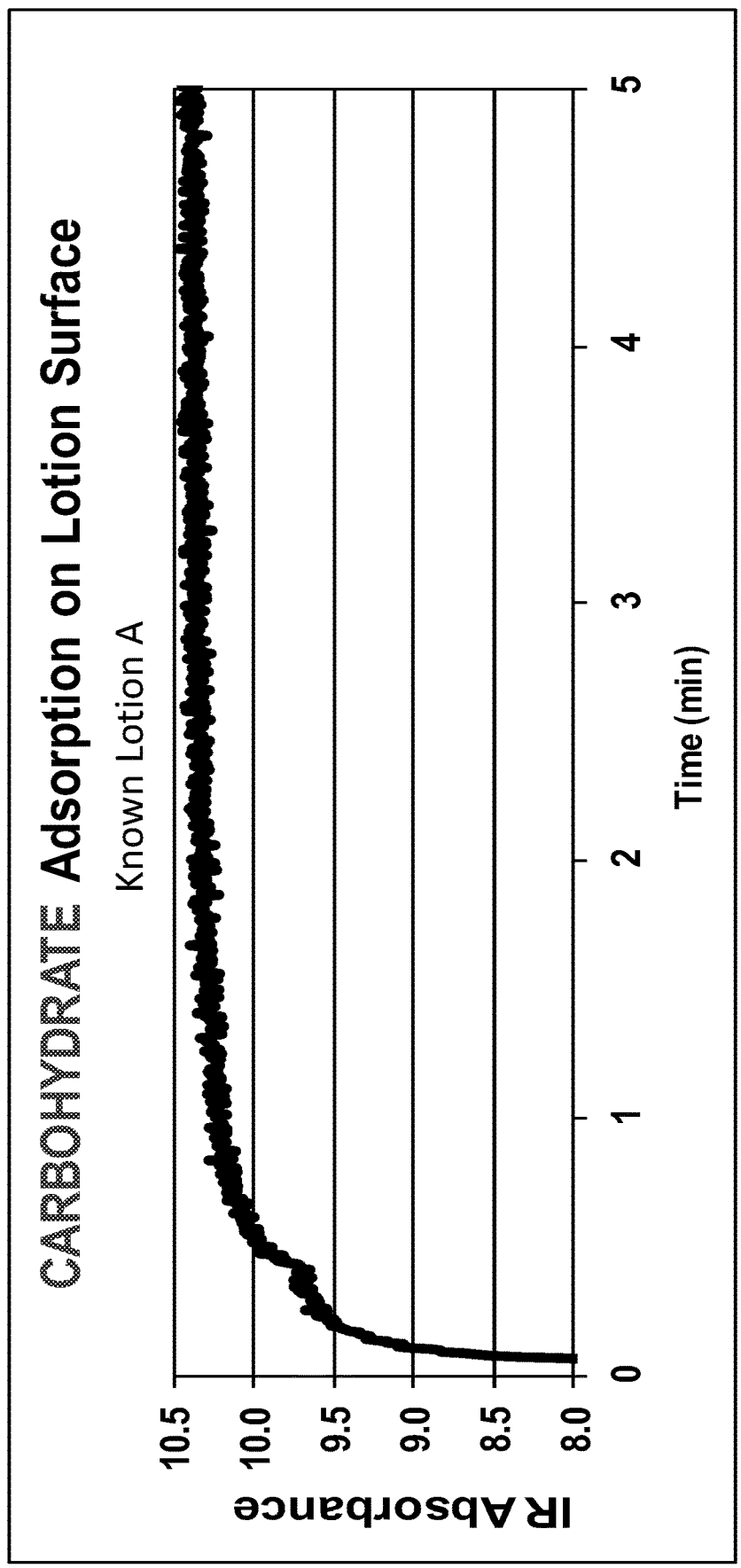
FIGS. 3a, b, and c show a plot of IR absorbance vs. time showing the reduced carbohydrate fouling achieved by a present lotion composition or a commercially used lotion.
Figure 3B:
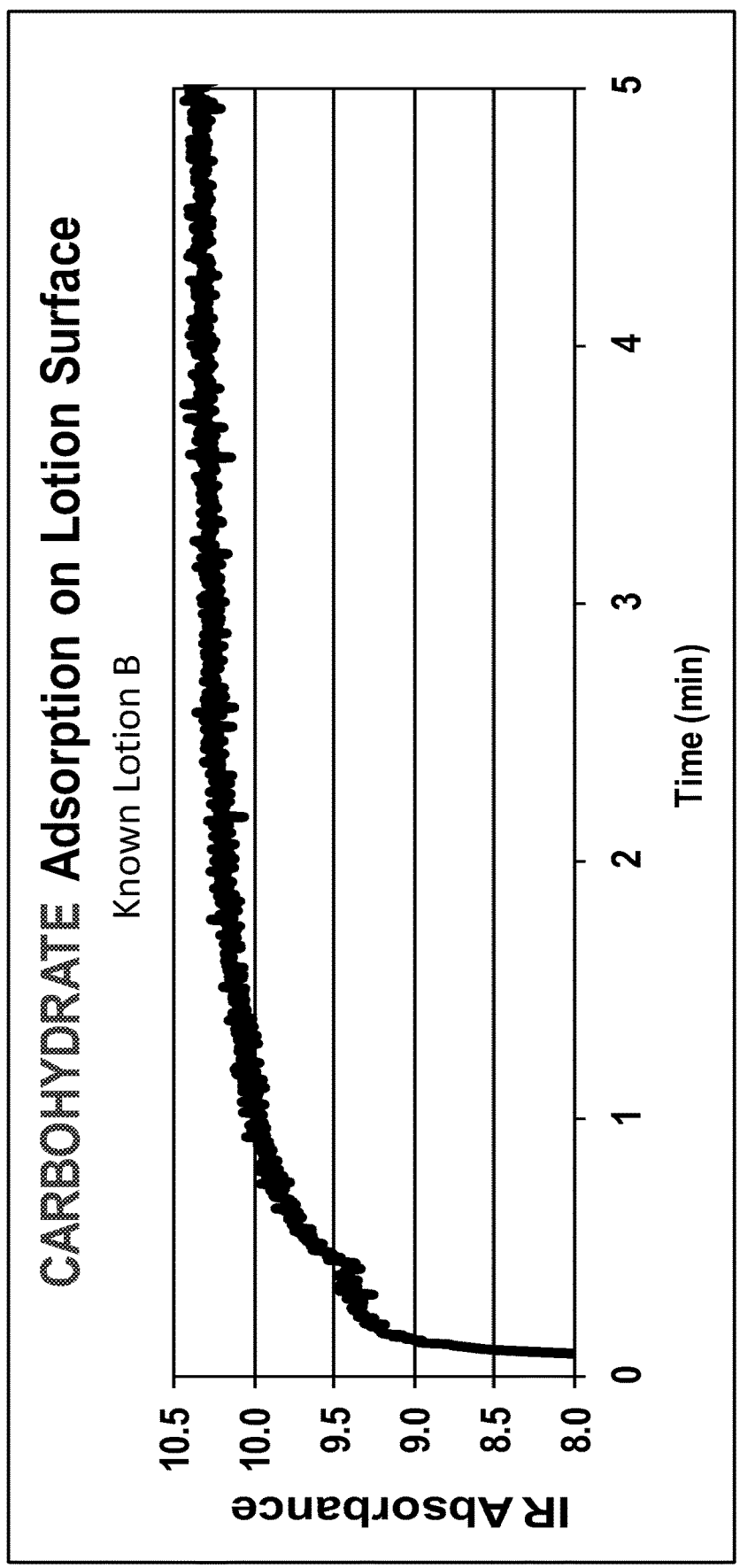
Figure 3C:
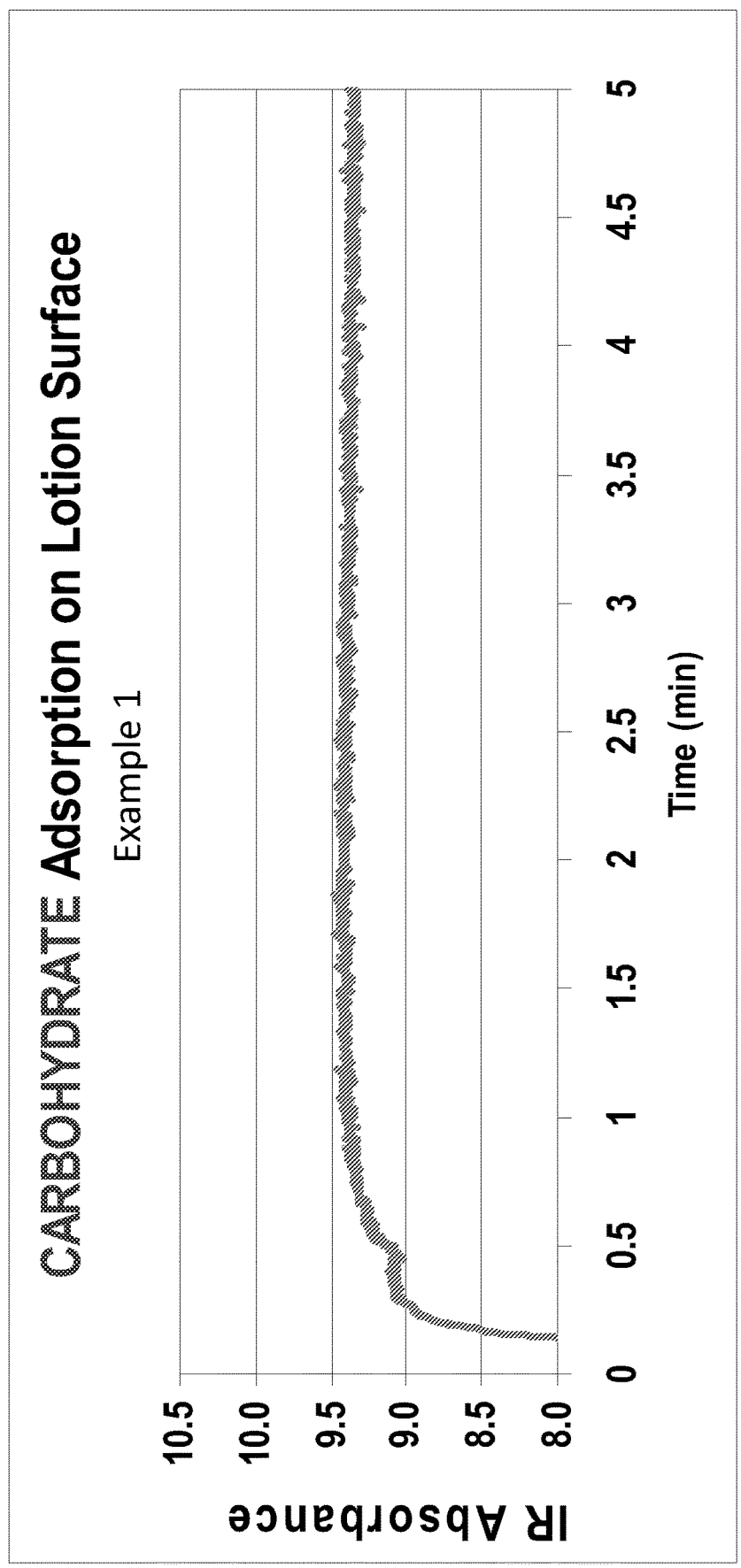
Figure 4A:
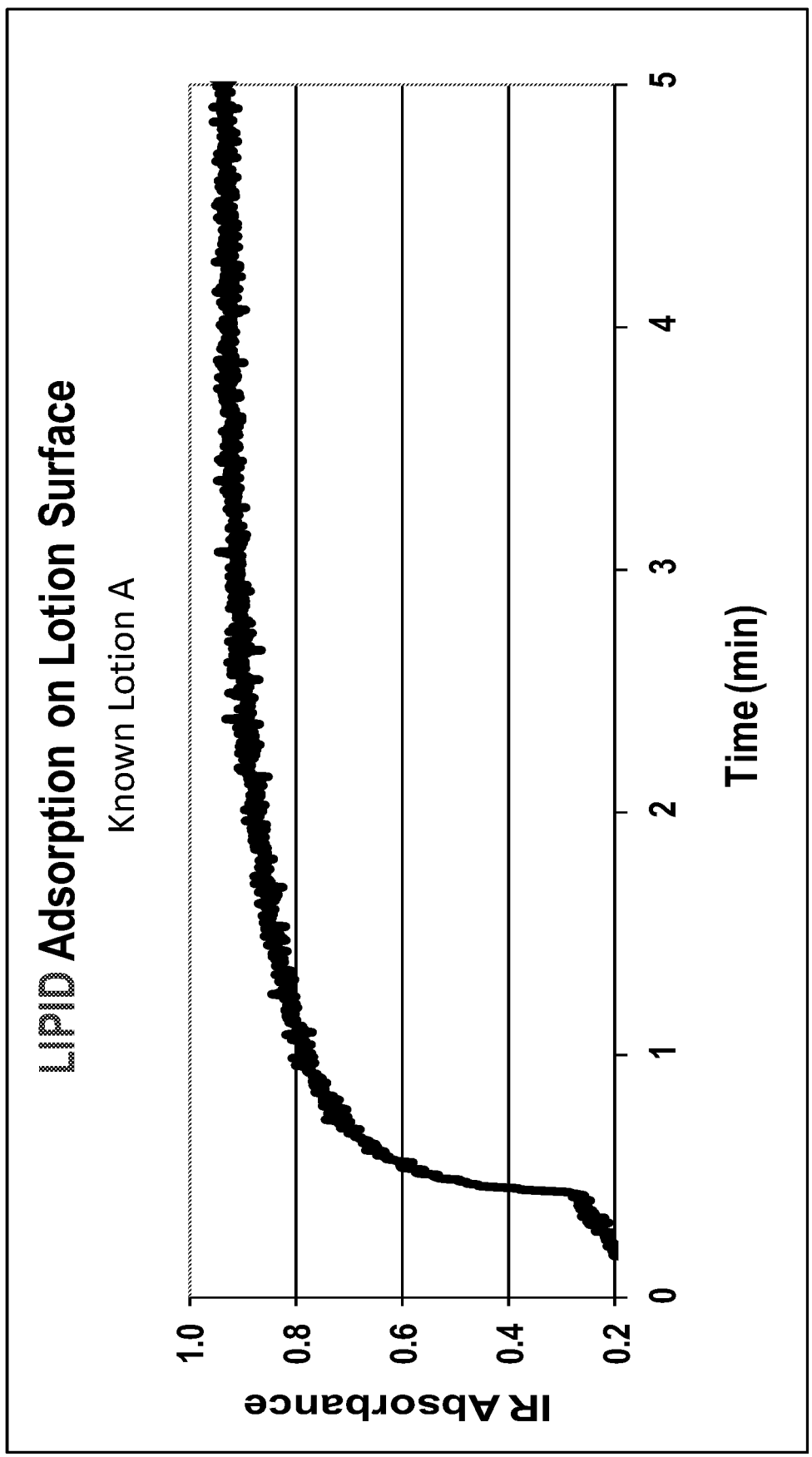
FIGS. 4a, b, and c show a plot of IR absorbance vs. time showing the reduced lipid fouling achieved by a present lotion composition or a commercially used lotion.
Figure 4B:
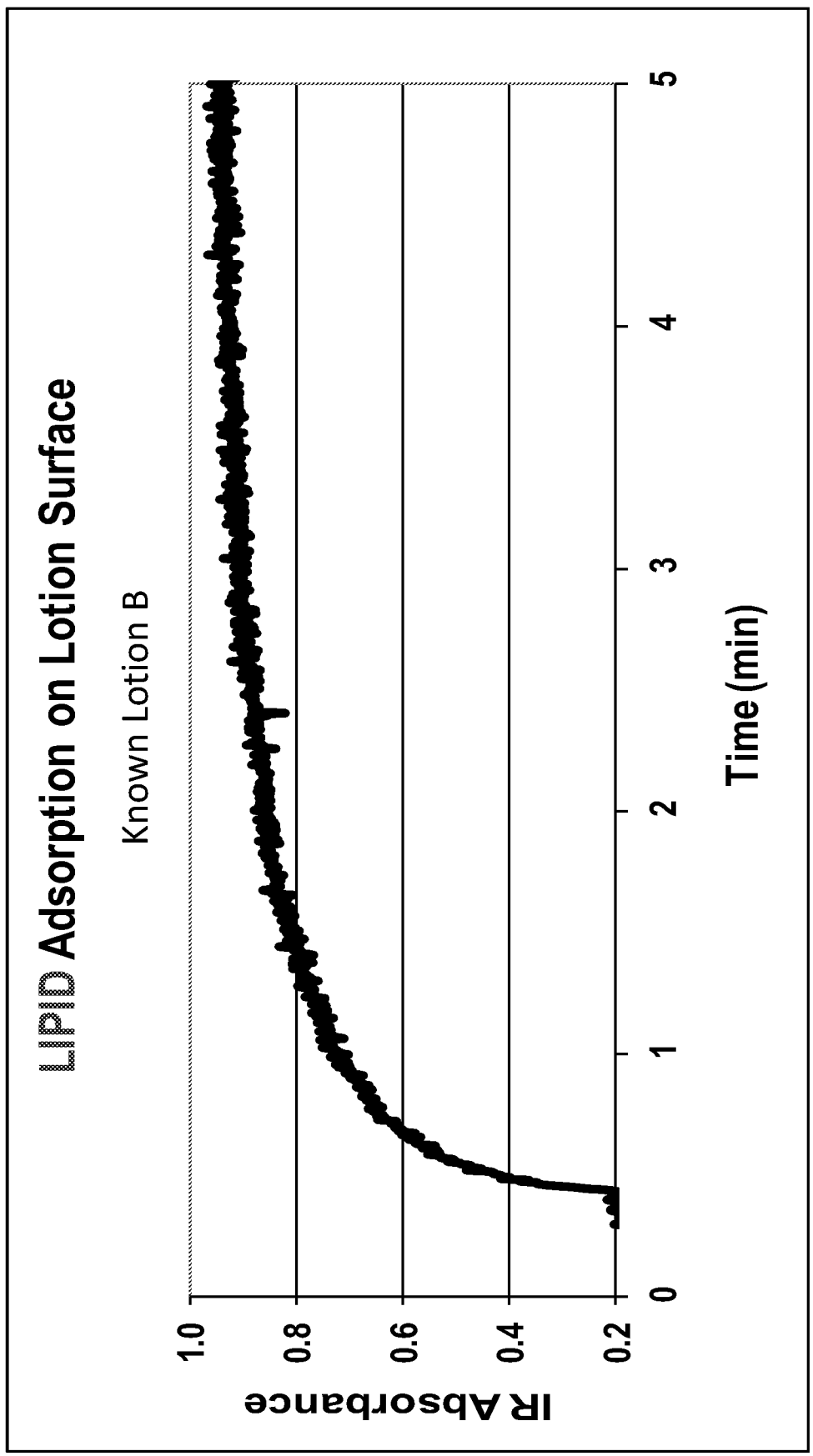
Figure 4C:
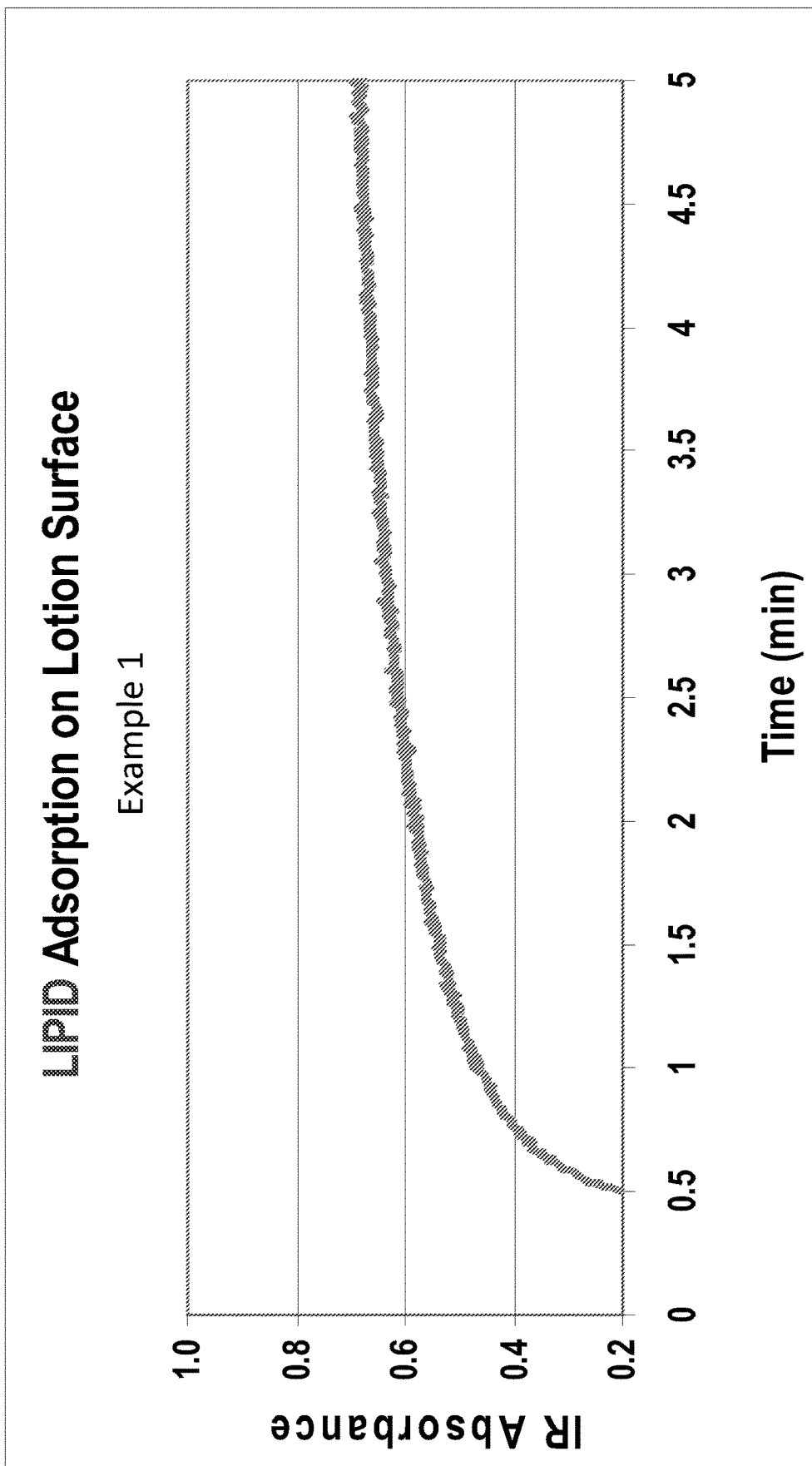

FIGS. 2-4 show three plots of IR absorbance vs. time (min) showing the reduced amount of surface fouling compounds absorbed by the lotion compositions of Example 1 compared to Known Lotion A and Known Lotion B. These results demonstrate that the lotion of Example 1 results in less surface adsorption of protein, carbohydrates, and lipids from a synthetic menstrual fluid as compared to Known Lotion A and Known Lotion B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A sanitary napkin comprising:
    a liquid pervious topsheet, said topsheet having an inner surface oriented toward the interior of said absorbent article and an outer surface oriented toward the skin of the wearer when said absorbent article is being worn;
    a backsheet joined to said topsheet, said backsheet having an inner surface oriented toward the interior of said absorbent article and an outer surface oriented toward the garment of the wearer when said absorbent article is being worn;
    an absorbent core disposed between said topsheet and said backsheet, said absorbent core having an inner surface oriented toward the skin of the wearer when said absorbent article is being worn and an outer surface oriented toward the garment of the wearer when said absorbent article is being worn;
    and a lotion composition applied to the topsheet, the lotion comprising:
        a rheology structurant
        a carrier; and
        a surface energy modifier comprising POE-4 monolaurate or POE-8 monostearate;
    wherein the lotion is semi-solid or solid at ambient, liquid or semi-solid at body temperature and liquid with processible viscosity at 60-90 C.

2. The sanitary napkin of claim 1, wherein the surface energy modifier comprises POE-4 monolaurate and POE-8 monostearate.

* * * * *